(12) United States Patent
Zandman

(10) Patent No.: US 6,332,862 B1
(45) Date of Patent: Dec. 25, 2001

(54) ARTICLES OF CLOTHING INCORPORATING MAGNETS FOR THERAPEUTIC PURPOSES

(76) Inventor: Michael Zandman, 6 Magnolia La., Colts Neck, NJ (US) 07722

( * ) Notice: Subject to any disclaimer, the term of this patent is extended or adjusted under 35 U.S.C. 154(b) by 0 days.

(21) Appl. No.: 09/469,003

(22) Filed: Dec. 21, 1999

(51) Int. Cl.$^7$ ............................... A61N 7/00; A41B 9/00
(52) U.S. Cl. ................................. 600/15; 2/109; 600/38
(58) Field of Search .................... 2/115, 159, 109; 24/303; 63/23; 351/158; 428/692; 450/38; 600/1.3, 9, 13, 15, 38

(56) References Cited

U.S. PATENT DOCUMENTS

| | | |
|---|---|---|
| 2,999,275 | 9/1961 | Blume, Jr. . |
| 4,134,405 | 1/1979 | Smit . |
| 4,162,672 | 7/1979 | Yazaki . |
| 4,313,438 | 2/1982 | Greatbatch . |
| 4,314,554 | 2/1982 | Greatbatch . |
| 4,737,710 | 4/1988 | Van Antwerp et al. . |
| 4,873,504 | 10/1989 | Blume, Jr. et al. . |
| 4,921,560 | 5/1990 | Yamaguchi . |
| 4,924,542 | 5/1990 | Yamaguchi . |
| 5,085,626 | 2/1992 | Frey . |
| 5,092,835 | 3/1992 | Schurig et al. . |
| 5,295,494 | 3/1994 | Rodriguez . |
| 5,424,703 | 6/1995 | Blume, Jr. . |
| 5,448,777 | 9/1995 | Lew . |
| 5,460,593 | 10/1995 | Mersky et al. . |
| 5,529,569 | 6/1996 | Woo . |
| 5,720,046 * | 2/1998 | Lopez et al. .............................. 2/159 |
| 5,782,671 * | 7/1998 | Suen et al. .............................. 450/38 |
| 5,782,743 | 7/1998 | Russell . |
| 5,817,000 * | 10/1998 | Souder .................................. 600/15 |
| 5,950,239 * | 9/1999 | Lopez ...................................... 2/115 |
| 5,965,282 * | 10/1999 | Baermann ............................ 428/692 |

* cited by examiner

Primary Examiner—Eric F. Winakur
Assistant Examiner—Nikita R Veniaminov
(74) Attorney, Agent, or Firm—Hedman & Costigan, P.C.

(57) ABSTRACT

Articles of clothing having magnets incorporated therein placed at areas corresponding to the small arteries and veins which supply blood to erogenous zones including the sex organs. The magnets can be permanently incorporated into the clothing with stitching or removably incorporated into the clothing with a pouch having overlapping sections or releasable means such as VELCRO, snaps or buttons.

19 Claims, 2 Drawing Sheets

ARTICLES OF CLOTHING INCORPORATING MAGNETS FOR THERAPEUTIC PURPOSES

FIELD OF THE INVENTION

The present invention relates to clothing into which magnets are incorporated to provide therapeutic effects to the wearer including improved sexual function.

BACKGROUND OF THE INVENTION

Recently, the use of magnets has become more common to provide physical therapeutic benefits to those who maintain an electric or magnetic field over a portion of their body. Electromagnetic treatments have been used where a headpiece which can generated a magnetic field is placed over the user's head to stimulate nerves in the neural pathway. See U.S. Pat. No. 5,092,835. Additionally, magnetic structures corresponding to accupressure points have been used in gloves to help sooth hands, as described in U.S. Pat. No. 5,720,046.

In more general cases, magnetic field generating devices have been incorporated into straps, bands, belts or the like so the magnetic field could be placed on various parts of a human body. See U.S. Pat. No. 5,529,569; 5,782,743; and 5,085,626.

In contrast to such adaptable devices for placing on many different specific portions of the body, others have described the use of mattresses and covers into which magnetic devices are provided to assist all ailments. See U.S. Pat. Nos. 4,921,560 and 4,924,542.

It is an object of the present invention to provide an improved method of delivering the therapeutic benefits of a magnetic field to a user.

It is also an object of the present invention to provide the magnetic field over a sustained, prolonged period of time.

It is a further object of the present invention to incorporate only sufficient magnetic sources to address specific deficiencies.

It is another object of the present invention to make use of the magnets comfortable by proper shape, flexibility and placement over the specific portions of the user's body.

SUMMARY OF THE INVENTION

These and other objects are achieved by the present invention which is directed to articles of clothing having magnets incorporated into the clothing where the magnets are placed into the clothing in an area corresponding to that of the small arteries and veins supplying blood to the erogenous areas including the sexual organs of the user.

The preferred articles of clothing for use in the present invention are undergarments such as briefs and brassieres.

Preferably, the magnets are attached to or sewn into the articles of clothing to maintain the magnets in the proper position over the areas of the small arteries and veins. In an alternative embodiment, the magnets can be placed into "pouches" on the garment so that they can be removed for laundering the garment or to make the magnets replaceable with stronger magnets once they begin losing their magnetic capacity.

The use of the garments of the present invention results in increased erections in males as well as improved sexual function and enjoyment in men and women. This effect has been enhanced when the wearer wears the garment of the present invention for extended periods, i.e., 8 hours or more.

BRIEF DESCRIPTION OF THE DRAWINGS

The attached drawings, wherein like reference characters indicate like parts, are provided for illustration purposes only. The drawings are not intended to limit the scope of the invention in any manner whatsoever.

DETAILED DESCRIPTION OF THE PREFERRED EMBODIMENT

Figure 1:
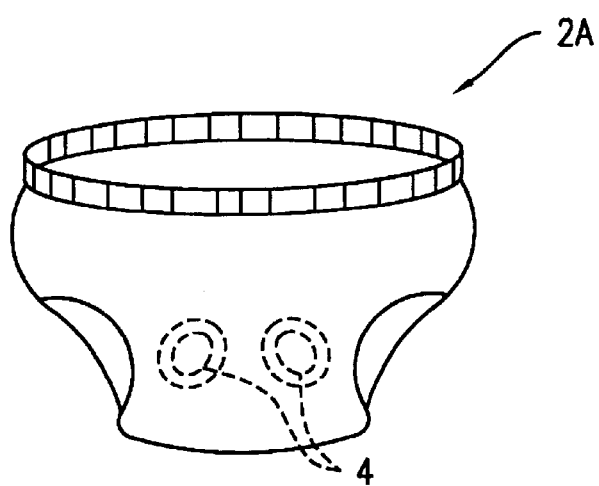
FIG. 1 is a front elevation of a pair of men's briefs incorporating magnets in a preferred placement for increasing blood flow to the male sex organ.
Figure 2:
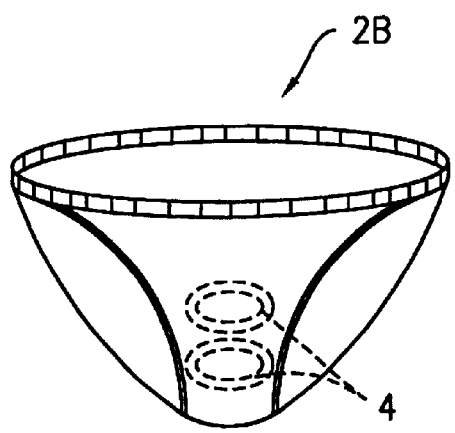
FIG. 2 is a front elevation of a pair of women's brief incorporating magnets in a preferred placement for increasing blood flow to the female sex organ.
Figure 3:
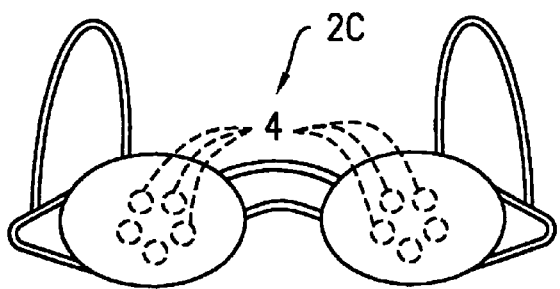
FIG. 3 is a front elevation of a brassiere incorporating magnets in preferred placement for increasing blood flow to a woman's areola.

In its most preferred embodiment, shown in FIGS. 1–3, the garment 2 includes one or more magnets 4 which are positioned over a specific portion of a user's body associated with the small arteries and veins which supply blood to erogenous zones including the sex organs.

In FIG. 1 the garment 2 is a pair of men's briefs 2A. The magnets 4 are preferably sewn into the area just above the male organ, most preferably one on each side in the lower abdominal area. This placement minimizes the number of magnets needed and, therefore, improves the comfort wherein the magnets are preferably flexible but practically are generally of limited flexibility and have hard edges.

Similarly in FIG. 2, which shows a women's briefs or panties 2B, the magnets are preferably placed over the female organ and, most preferably in the pelvic area.

As shown in FIG. 3, a women's brassiere 2C includes magnets around the areola. This placement is also used to increase blood flow for increased sensitivity and stimulation.

The garments 2 can be made of any commonly used material such as cotton, silk, nylon, polyester and/or blends of these or other materials. Of course, the material and the attachment of the magnets 4 to the garment 2 should be comfortable to the wearer.

Preferably, the magnets 4 are at least somewhat flexible and/or adaptable or contoured to the user's anatomy. It is also preferred that the magnet is thin, i.e. in the range of about 0.01 to about 0.25 inches, to provide comfort to the user. Most preferably, the magnets 4 are rubber bonded such as the PLASTALLOY™ rubber bonded strontium ferrite permanent magnets, from The Electrodyne Company, Inc. of Batavia, Ohio, available in strip form which can be cut to size. The polarity can be conventional single polarity on each side, two poles on each side or multiple alternating poles on each side. Alternatively, flexible bonded neodymium iron boron permanent magnets can be used, such as Reance F™ magnets also from The Electrodyne Company, Inc., or any suitable magnet.

Figure 4:
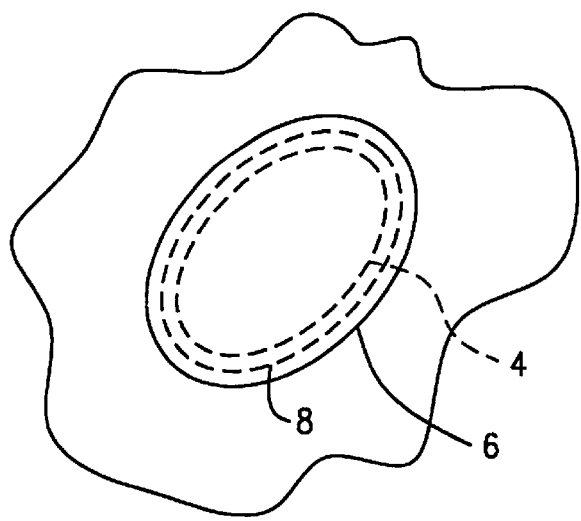
FIG. 4 is a detail of a magnet stitched into a garment.
Figure 4A:
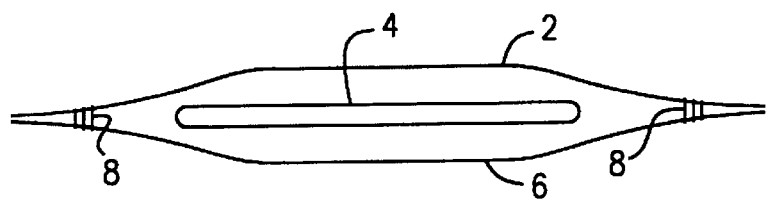
FIG. 4A is a cross section of a magnet stitched into a garment.

In its most simple embodiment, shown in FIG. 4, the magnet 4 is attached to the garment 2 by placing a patch 6 over the magnet 4 and sewing the perimeter of the patch 6 with stitches 8 to hold the magnet 4 between the garment 2 and the patch 6. See FIG. 4A. Similarly, a second layer can be used across a portion of the garment 2 having more than one magnet 4 and the individual magnets 4 can be stitched around to maintain proper placement.

Figure 5:
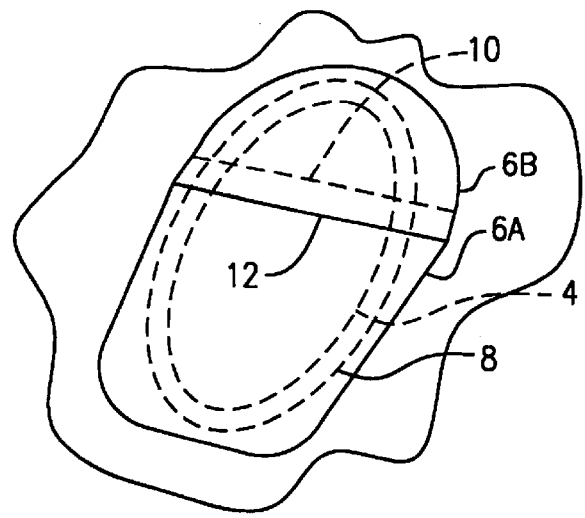
FIG. 5 is a detail of a preferred pouch for removably holding a magnet.

In an alternative embodiment, shown in FIG. 5, the patch 6 covering the magnet 4 includes a first patch section 6A and a second patch section 6B which are overlapped and sewn about the perimeter with stitches 8. In this embodiment, the first patch section 6A terminates at interior edge 10 which extends beyond the exterior edge 12 of section 6B to form an overlap. Thus, if the user wishes to remove the magnet 4 from the garment 2, exterior edge 12 is pulled up over interior edge 10 and the magnet 4 can be removed.

Other variations include the use of snaps, buttons, hook and loop-type fastener (VELCRO) or similar attachment means which can secure a patch-type opening as described above to prohibit the magnet 4 from falling out unintentionally but can be pulled apart to remove the magnet 4. The magnets 4 can alternatively be attached directly to the garment 2 by such means as VELCRO, snaps, clips or the like to be removable, or adhered directly to the garment 2 to minimize costs of production.

Other such apparent deviations will be known to those skilled in the art who review this invention. All such variations are intended to fall within the spirit and scope of the present invention, limited solely by the attached claims.

All patents cited herein are incorporated by reference.

What is claimed is:

1. An article of clothing for use by a wearer having one or more magnets incorporated therein, the one or more magnets being maintained in the areas consisting essentially of those corresponding directly to the areas of the small arteries and veins which supply blood to the erogenous zones of the body.

2. The article of clothing as in claim 1 wherein the erogenous zones corresponding to the small arteries and veins where the magnets are placed are associated with the sex organs.

3. The article of clothing of claim 1 being underclothing.

4. The article of clothing of claim 3 being men's briefs.

5. The article of clothing of claim 3 being women's briefs or panties.

6. The article of clothing of claim 3 being a brassiere.

7. The article of clothing of claim 1 wherein the magnets are removable from and replaceable in the article of clothing.

8. The article of clothing of claim 1 wherein the article of clothing includes a pouch into which at least a portion of one of the one or more magnets is removably inserted.

9. The article of clothing of claim 1 wherein at least one of the one or more magnets is incorporated into the article of clothing by an incorporation member taken from the group consisting of overlapping patch sections, hook and loop-type fastener, snaps, buttons and combinations of the foregoing.

10. The article of clothing of claim 1 wherein the magnets are flexible.

11. The article of clothing of claim 10 wherein the magnets are rubber bonded permanent magnets.

12. A method of improving sexual function comprising wearing an article of clothing having magnets incorporated therein, said magnets corresponding to the areas of the small arteries and veins which supply blood to a wearer's sexual organs, over a sustained period of 8 or more hours.

13. An article of clothing for use by a wearer having one or more flexible magnets incorporated therein, the one or more magnets being maintained in the areas consisting essentially of those corresponding directly to the areas of the small arteries and veins which supply blood to the erogenous zones of the body, the article of clothing being flexible in areas corresponding to the one or more flexible magnets.

14. The article of clothing of claim 13 wherein the article of clothing is underclothing.

15. The article of clothing of claim 14 wherein the article of clothing is taken from the group consisting of men's briefs, women's briefs or panties and brassieres.

16. The article of clothing of claim 13 wherein the one or more flexible magnets are removable from and replaceable in the article of clothing.

17. The article of clothing of claim 13 wherein the article of clothing includes a pouch into which at least a portion of the one or more magnets is removably inserted.

18. The article of clothing of claim 13 wherein at least one of the one or more magnets is incorporated into the article of clothing by an incorporation member taken from the group consisting of overlapping patch sections, hook and loop-type fastener, snaps, buttons and combinations of the foregoing.

19. The article of clothing of claim 13 wherein the at least one flexible magnet is a rubber bonded permanent magnet.

\* \* \* \* \*